United States Patent [19]

Sekino et al.

[11] Patent Number: 4,977,902
[45] Date of Patent: Dec. 18, 1990

[54] SUPERSONIC HYPERTHERMIA TREATING METHOD

[75] Inventors: Naomi Sekino; Shuichi Takayama; Takashi Tsukaya, all of Hachioji; Masakazu Gotanda, Kanagawa; Tetsumaru Kubota, Hachioji; Naoki Uchiyama, Hachioji; Koichiro Ishihara, Hachioji; Kuniaki Kami, Hachioji; Akira Murata, Hachioji; Masaaki Hayashi, Hachioji, all of Japan

[73] Assignee: Olympus Optical Co., Ltd., Japan

[21] Appl. No.: 348,814

[22] Filed: May 8, 1989

[30] Foreign Application Priority Data

Jul. 15, 1988 [JP] Japan ............................. 63-176323

[51] Int. Cl.⁵ ............................................. A61N 1/06
[52] U.S. Cl. ............................. 128/804; 128/422; 128/24 AA
[58] Field of Search ............... 128/399, 400, 422, 804, 128/24 AA; 600/12, 13

[56] References Cited

U.S. PATENT DOCUMENTS

| 4,323,056 | 4/1982 | Borrelli | 128/804 |
| 4,397,314 | 8/1983 | Vaguine | 128/399 |
| 4,448,198 | 5/1984 | Turner | 128/422 |
| 4,652,257 | 3/1987 | Chang | 600/12 |
| 4,712,559 | 12/1987 | Turner | 128/399 |
| 4,785,824 | 11/1988 | Wickersheim et al. | 128/804 |
| 4,827,945 | 5/1989 | Groman et al. | 500/12 |
| 4,908,011 | 3/1990 | Jacobsen et al. | 600/12 |

Primary Examiner—Edward M. Coven
Assistant Examiner—Valerie Szczepanik
Attorney, Agent, or Firm—Ostrolenk, Faber, Gerb & Soffen

[57] ABSTRACT

A supersonic hyperthermia treating method comprises the steps of inserting a heat generating member having a high attenuation for supersonic waves into a diseased part in a body and leaving it there, then transmitting supersonic waves generated outside of the body from a supersonic wave generator for heating the heat generating member to hyperthermically treat the diseased part.

29 Claims, 8 Drawing Sheets

006
SUPERSONIC HYPERTHERMIA TREATING METHOD

FIELD OF THE INVENTION AND RELATED ART STATEMENT

The present invention relates to a supersonic frequency hyperthermia treating method in which a diseased part such as a tumor in a body is irradiated with a high supersonic energy for hyperthermically treating the diseased part. As used herein, the term "supersonic" refers to the frequency of the radiation applied in treatment.

Hyperthermia treating method is one of the methods for treating tumors, cancer and the like formed in a body. This treating method uses a fact that cancer cells and the like are weakened by heat. For example, cancer cells are distroyed at a temperature not less than 43° C. The diseased part is irradiated with high energy supersonic waves or radio frequency waves such as microwaves which are generated outside of a body so that the diseased part is heated.

The summary of the structure of a supersonic treating apparatus will be described with reference to FIG. 22. The supersonic treating apparatus comprises observation means (position detection means) for detecting the position of the diseased part in a body, positioning signal generating means 4, focus moving means 7 and supersonic oscillator driving means 11.

The observation means comprises a supersonic observation device 2 for detecting the position of the diseased part such as a tumor or the like, in a body by radiating supersonic waves upon a human body 10 and a display device 3 which displays the position of a diseased part on a display such as CRT in response to a detection signal from the observation apparatus.

The positioning signal generating means 4 provides an indication marker and the like at an aimed point on the display device 3 and outputs a control signal to a focus moving means 7 so that the focus of the supersonic wave generator 6 coincides with the indication marker position. That is, the positioning signal generating means 4 is adapted to process the image of the diseased part, the position of which is detected. The surgical operator such as medical doctor recognizes the dimension and depth of the displayed diseased part and interacts with the display of the display device 3 by means of a light pen or the like to provide a positioning signal for performing the most effective treatment and then stores the treatment sequence. The positioning signal generating means 4 provides the focus moving means 7 with the positioning signal when the treatment is conducted.

The focus moving means 7 moves a water bag 5 and the supersonic wave generator 6 in accordance with the positioning signal by means of numerical control robot, or the like, for focusing the supersonic wave upon the diseased part. The supersonic wave generator 6 comprises a multiplicity of supersonic oscillators including piezoelectric elements which are mosaically disposed on the front face of a mounting plate 9 which is formed into a spherical shape. The generator 6 is disposed so that the front supersonic wave generating face is directed towards a human body 10. Between the supersonic wave generator 6 and the human body 10 is disposed the water bag 5 made of a flexible resin or the like, having liquid charging and pressure control means. The bag 5 is filled with an supersonic wave transmitting liquid such as water.

The thus formed supersonic treating apparatus generates supersonic waves from the supersonic wave oscillator 8 after it causes the focus of the supersonic wave generator 6 to coincide with the diseased part. A very strong supersonic wave sound field is formed at the focus position, that is at, the diseased part, so that the diseased part is heated to provide treatment.

Since the energy generated in the supersonic wave oscillator 8 is converted into heat even in the oscillator or the transmitting medium, temperature elevation of those elements occurs, resulting in a low efficiency. The heat generation is low since the supersonic wave is not largely attenuated in water or muscle layer of a human body. Therefore, in order to obtain a high supersonic wave energy, high power should be employed, resulting in an increase in heat loss and low heat generating efficiency.

It is to be noted that supersonic waves cause high heat generation in a material having a large attenuation. If a material having a high attenuation for supersonic waves is disposed at a part to be treated, such as tumor, which will respond therapeutically to heat treatment, it is possible to selectively heat only the part to be treated by using even a low power supersonic wave.

OBJECT AND SUMMARY OF THE INVENTION

It is an object of the present invention to provide a supersonic hyperthermia treating method in which a heat generating member having a high supersonic wave attenuation is disposed at a part to be treated in a body, which is to be irradiated with a supersonic wave from the outside of the body.

Since a heat generating member having a high attenuation for supersonic waves is inserted into and left at a part to be treated in a body in accordance with the present invention, even a low power supersonic wave causes the heat generating member to sufficiently generate heat, to make it possible to conduct very efficient hyperthermia treatment.

DETAILED DESCRIPTION OF PREFERRED EMBODIMENTS

Figure 1:
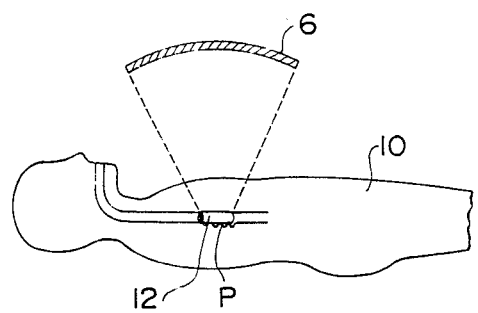
FIG. 1 is a schematic view of a first embodiment of the present invention showing how a supersonic hyperthermia treatment is conducted.
Figure 22:
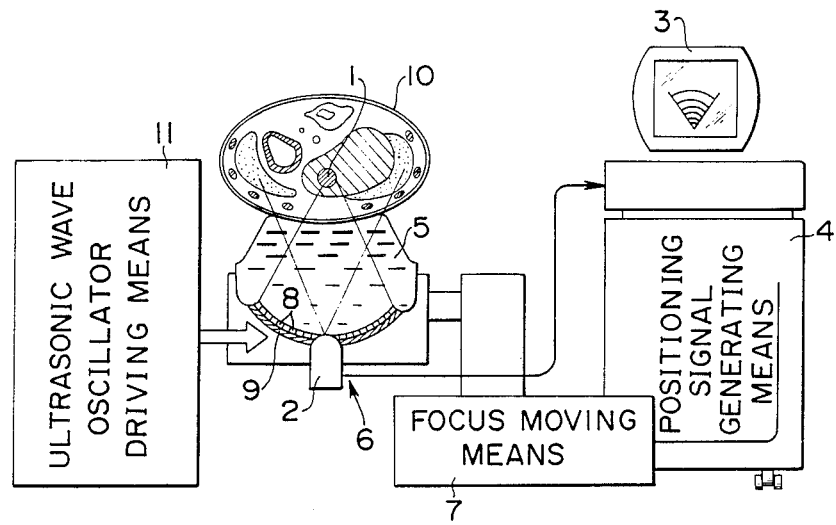
FIG. 22 is a schematic view showing the general structure of a supersonic wave treating apparatus.

Referring now to FIG. 1, a first embodiment of a supersonic hyperthermia treating method of the present invention will be described. A heat generating member 12 formed of a polymeric material applicable to a living body and having high attenuation for supersonic wave such as silicon rubber, polyethylene, acrylic resins, ethylene tetrafluoride, etc. is inserted through an endoscope into and left at a diseased part P where, for example, a tumor or the like is formed in a body. Thereafter, the focus position of a supersonic wave generator 6 of a supersonic hyperthermia treatment apparatus is brought into coincidence with the heat generating member 12. If supersonic waves are then generated, the generated supersonic waves are focussed upon the heat generating member 12 so that the supersonic wave is largely attenuated in the heat generating member, resulting in intense heat generation from the member. Accordingly, the diseased part is hyperthermically treated by this heat. In this case, a low driving power input into supersonic oscillators 8 (refer to FIG. 22) of a treating apparatus suffices. The heat generating member 12 which is to be left may be formed of various polymeric materials depending upon the size of tumor and its position. The various polymeric materials should be compatible for use in intra-abdominal organs such as esophagus, colon, bile duct, uretha, ureter, uterus and liver.

Figure 2:
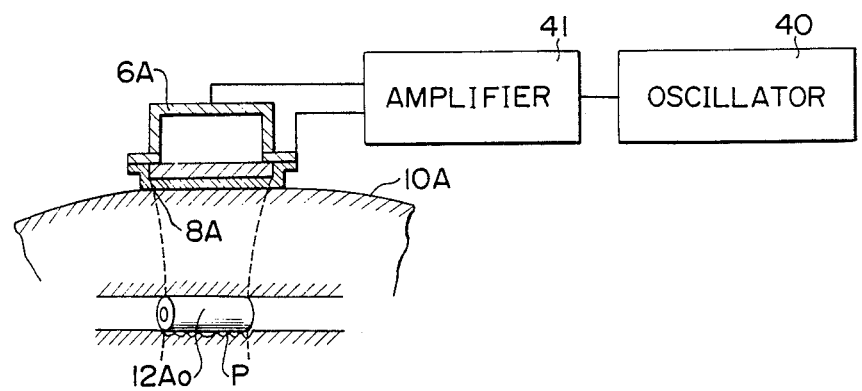
FIG. 2 is a schematic view of a second embodiment of the present invention showing how a supersonic wave hyperthermic treatment is conducted.

FIG. 2 shows a second embodiment of a supersonic hyperthermia treating method of the present invention. The heat generating member 12A$_0$ which was left at the diseased part P in a body 10A is irradiated with supersonic waves generated from the supersonic wave generator 6A having a flat oscillator 8A including piezoelectric elements without focusing the supersonic wave upon the heating member 12A$_0$ in the second embodiment while the supersonic wave which has been emitted from the outside of a body is focused upon the heat generating member 12 in the first embodiment. Driving pulses which are generated in an oscillator 40 are amplified in an amplifier 41 and are applied to the flat oscillator 8A.

In such a manner the heat generating member 12A$_0$ generates enough heat even by irradiating the heating member with supersonic waves without focusing the same upon the member 12A$_0$.

Figure 3:
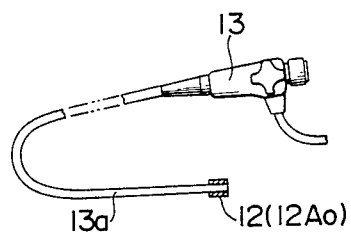
FIG. 3 is a perspective view showing an example of means for inserting a heat generating member into a body cavity.
Figure 4:
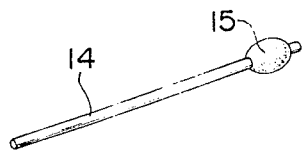
FIGS. 4 and 5 are perspective views showing other respective means for inserting a heat generating member into a body cavity.

In the above embodiment, the heat generating member 12, 12A$_0$ is left at the diseased part P. The heat generating member 12, 12A$_0$ made of above-mentioned polymeric material is mounted upon the outer periphery of a tip end of body cavity insertion portion 13a of an endoscope 13 or the outer periphery of the tip end of a catheter to be inserted into a body cavity as shown in FIG. 3. The heat generating member 12, 12A$_0$ is disposed at the diseased part by inserting the endoscope 13 or catheter into a body cavity. The inserted heat generating member 12, 12A$_0$ may be irradiated with supersonic waves from the supersonic wave generator 6, 6A. A balloon 15 made of extensible elastomeric material, such as latex or silicon rubber which is mounted upon the tip end of the balloon catheter 14, is used as a heat generating member having a high supersonic wave attenuation and is inserted into a body cavity having diseased part. The balloon 15 is irradiated with supersonic waves so that it may be sufficiently heated. Since the balloon 15 can be brought into intimate contact with the diseased part formed on the inner wall of the body cavity by inflating the balloon 15 when the balloon is used, the heating efficiency can be further improved.

Figure 5:
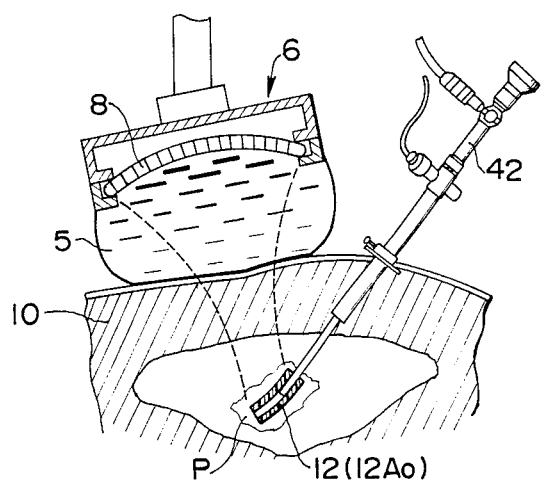

FIG. 5 shows more another example of means for inserting and leaving the heating member 12, 12A$_0$. In this case, a well-known rigid endoscope 42 such as that known as a rigidscope which may be a laparoscope or a peritoneoscope is used. The heat generating member 12, 12A$_0$ is mounted upon the tip end of the rigidscope 42. The heat generating member is left at a diseased part in a cavity within a human body 10 by means of the rigidscope 42 which is inserted into the body by cutting the surface of the human body. Thereafter, supersonic waves generated by supersonic oscillator 8 in the supersonic generator 6 are directed to the heat generating member 12, 12A$_0$ via a water bag 5. It is apparent that the rigidscope 42 may be a uretercystoscope as well as laparoscope.

Figure 6:
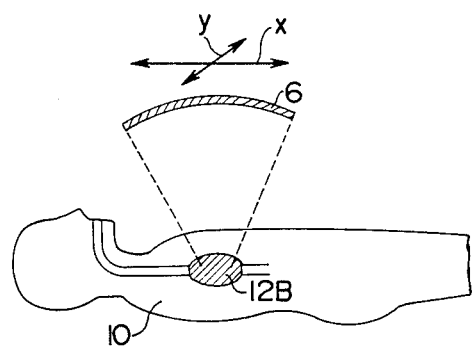
FIG. 6 is a schematic view of a third embodiment of the present invention showing how a supersonic hyperthermia treatment is conducted.

FIG. 6 shows a third embodiment of the present invention. In this embodiment, a gel material having a high attenuation for supersonic waves, such as silcon gel is used as a heat generating member 12B. The gel is injected into a diseased part in a body cavity of a human body 10 through an endoscope so that the diseased portion is filled with the gel material. The gel material is irradiated with supersonic waves by means of supersonic wave generator 6. At this time, the supersonic wave generator 6 is swept in directions as shown by arrows X and Y. Since this makes it possible to heat the part to be treated over a wide range thereof, efficient treatment is possible if the part to be treated is wide. After the treatment, the gel heat generating member 12B may be removed from the human body by means of a vacuum device.

Figure 7:
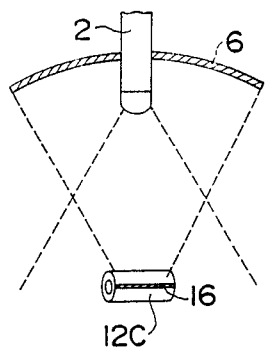
FIG. 7 is a schematic view of a fourth embodiment of the present invention showing how a heat generating member is observed in a supersonic hyperthermia treating method.

FIG. 7 shows a fourth embodiment of the present invention. In this embodiment, a heat generating member 12c made of a polymeric material which is inserted into a body through an endoscope and is left at a diseased part in the body as is similar to the embodiment 1 (refer to FIG. 1) is designed in such a manner that a part of the heating member 12c is formed with markings 16 made of metal or air layer. The markings are made of a metal (for example, stainless steel or air layer having an acoustic impedance largely different from that of the heat generating member 12c.

Since the position of the heat generating member 12c which is left is indicated in a slice image by detecting the marking 16 when an observatory supersonic wave is emitted by means of supersonic observatory apparatus 2 (refer to FIG. 22), it can be detected whether or not the position of the heat generating member 12c is shifted from the diseased part.

In order to detachably adapt the cylindrically formed heat generating member 12, $12A_0$ made of a polymeric material to the outer periphery of a tip end of a body cavity insertion portion of an endoscope or the outer periphery of a catheter and to insert the body cavity insertion portion or the catheter into a body cavity and to leave the heat generating member 12, $12A_0$ at the diseased part, the heat generating member 12, $12A_0$ should be prevented from detaching from the outer periphery of the body cavity insertion portion or the outer periphery of the tip end of the catheter until the heat generating member 12, $12A_0$ is transported to the part to be treated.

Figure 8A:
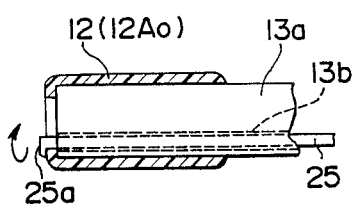
FIGS. 8A, 8B, 9, 10, 11A and 11B are enlarged sectional views showing alternative means for detachably mounting a heat generating member on the outer periphery of the front end of a body cavity insertion portion of an endoscope.
Figure 8B:
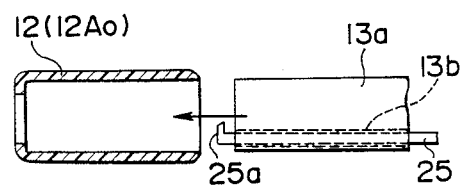

FIGS. 8A and 8B show an example of means for mounting the heat generating member. As shown in FIG. 8A, the heat generating member 12, $12A_0$ of a short cylinder which is loosely fitted to the tip end of a body cavity insertion portion 13a of an endoscope prevented from being detached from the tip end by means of fastener 25 having a hook 25a at the tip end thereof, which passes through a treating device insertion channel 13b of the endoscope, the hook 25a being engaged with a part of the end face of the member 12 or $12A_0$. After the heat generating member 12. 12A has been transported to a part to be treated under such a condition, the engagement of the member with the fastener 25 is released by rotating the fastener 25. The insertion portion 13a is moved in a detaching direction so that the heat generating member 12, 12A is detached from the tip end of the insertion portion 13a and is left there.

Figure 9:
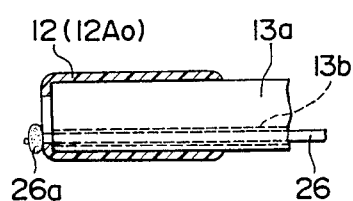

FIG. 9 shows another example of means for mounting. In this case, a balloon type catheter is used. That is, the balloon type catheter 20 is inserted through the treating device insertion channel 13b of an endoscope and is pressed down upon a part of the tip end face of the heat generating member 12, $12A_0$ of a short cylinder which is loosely fitted to the outer periphery of the tip end of the body cavity insertion portion 13a by inflating the balloon 26a at the tip end of the catheter, so that the heat generating member 12, $12A_0$ is prevented from being detached from the catheter 26. When the heating member 12 12A has been transported to the diseased part, the balloon 26a is deflated to release the pressing of the member upon the end face to allow the heat generating member 12, $12A_0$ to be detached from the catheter 26.

Figure 10:
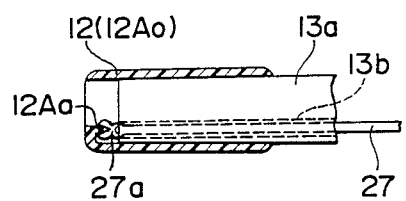

FIG. 10 shows another example of mounting means. In this case, well-known gripping forceps are used as a treating device of an endoscope. A heat generating member 12, $12A_0$ comprising a short cylinder formed of a polymeric material is provided with a projection 12Aa at a part of the tip end edge thereof. Detaching of the heat generating member 12, $12A_0$ is prevented by sandwiching the projection 12Aa with forceps portions 29a of a gripping forceps 27 which passes through a treating device insertion channel 13b of a body cavity insertion portion 13a. The heat generating member 12, $12A_0$ is detached from the insertion portion 13a by opening the foceps portions 27a.

Figure 11A:
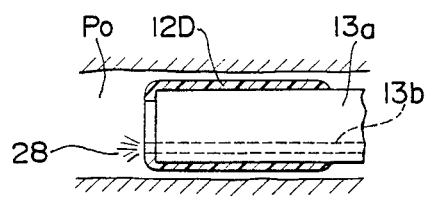
Figure 11B:
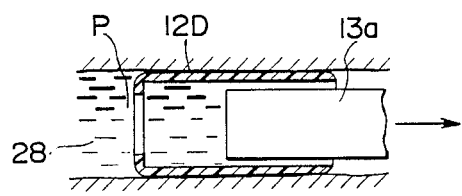

The mounting means may be formed as shown in FIGS. 11A and 11B. That is, the heat generating member 12D is formed into a short cylinder made of a shape memory polymer including polystyrene resins or polyurethane resins having a shape memory function. The member is dimensioned to have such a diameter so that it is firmly disposed on the tip end of the body cavity insertion portion 13a at a room temperature. Since detaching is prevented due to firm fitting while the member 12D is on the tip end of the insertion portion 13a, as shown in FIG. 11A, the heat generating member 12D may be transported to a position P in a body cavity when the member 12D reaches at the part P to be treated, warm water 28 is poured into it through a treating device insertion channel 13b of the endoscope. Then this causes the heat generating member 12D to expand and to be detached from the insertion portion 13a. The heat generating member may be left at the part P to be treated if the insertion portion 13a is removed as shown in FIG. 11B. An aspect of this mounting means is that the heat generating member 12D can be prevented from shifting from a leaving position since the inflated heat generating member 12D can be fitted to the wall of the body cavity.

Figure 12:
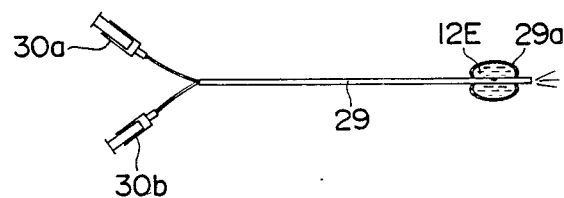
FIGS. 12 and 13 are views showing means for leaving a heat generating member at a diseased part using a balloon type catheter.

FIG. 12 shows means for leaving a heat generating member by using a well-known balloon catheter. In this case, a fluid having a high heat release value, for example, a highly viscous liquid such as castor oil or glycerin is used for the heat generating member. In lieu of a gas usually used for inflating a balloon 29a, a heat generating member 12E made of the above fluid is introduced through a channel in a catheter 29 by means of syringe barrel 30a to inflate the balloon and is left with the balloon 29a. In such a manner if the balloon type catheter 29 is used, anti-cancer compound and contrast medium can be introduced to a treating position by another syringe barrel 30b through another channel in the catheter 29 simultaneously with the introduction of the heat generating member.

Figure 13:
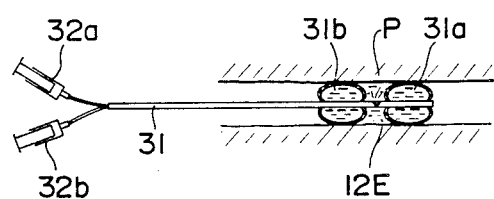

A heat generating member 12E may be left by using a well-known double balloon type catheter 31 as shown in FIG. 13. In this case, fluid such as highly viscous liquid having a high heat release value is also used as heat generating member 12E. A catheter 31 is, in advance, inserted into a body cavity. Balloons 31a and 31b are inflated at both sides of a treating position P are inflated with gas which is introduced through the other channel in the catheter 31 from a syringe barrel 32a so that they are pressed upon the body cavity wall to form a closed chamber including a treating position P. Thereafter, the heat generating member 12E of fluid is introduced through another channel in the catheter 31 from a syringe barrel 32b so that the closed chamber is filled with the heat generating member 12E from a channel opening located in the closed chamber. This can cause the heat generating member 12E to be left at the treating position P.

Figure 14A:
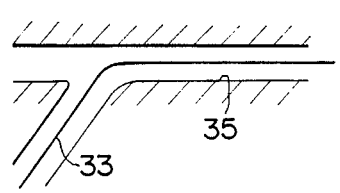
FIGS. 14A and 14B are side views showing a guide wire for inserting a heat generating member into a body cavity.
Figure 14B:
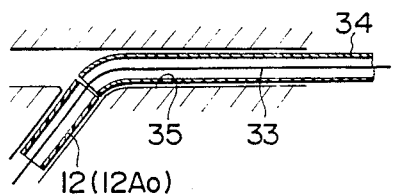

FIGS. 14A and 14B shows another example of means for inserting a heat generating member 12, 12A of a short cylinder made of a polymeric material into a treating position in a body cavity. A guide wire 33 is preliminarily inserted into a body cavity channel 35 through a treating device inserting channel of an endoscope as shown in FIG. 14A. Thereafter the short cylindrical heat generating member 12, $12A_0$ is inserted onto the guide wire 33 from outside. The rear end of the heat generating member is pressed by a pressing tube 34 having a diameter the same as that of the heat generating member $12A_0$ to transport the heat generating member 12, $12A_0$ to a treating position as shown in FIG. 14B.

As described in the above embodiments, in order to hyperthermically treat a diseased part, it is necessary to read the temperature of the heat generating member, 12, $12A_0$, 12A, 12B, 12C, 12D and 12E which hyperthermically treats the diseased part. There is a complicated method to compute the temperature at the deep part in a body which is heated by the irradiation with supersonic waves which is based on a change in sonic wave speed. But the temperature in a body may be simply measured by using the heat generating member in accordance with the present invention.

In other words, the heat generating member 12, $12A_0$, 12A, and 12C is made of a shape memory polymer such as polystyrene resins or polyurethane resins having a shape memory function. The change in shape due to change in temperature of the member is detected from outside by means of detector such as supersonic wave probe to read the temperature.

Figure 15:
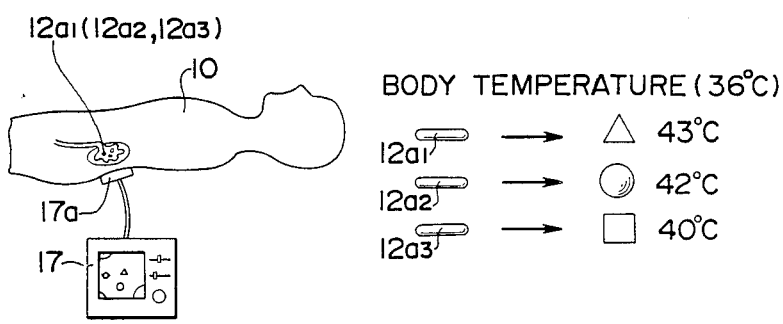
FIG. 15 is an explanatory view showing an example of means for detecting the temperature of a heat generating member.

FIG. 15 shows an example of a temperature detecting means. Heat generating members $12a_1$, $12a_2$, and $12a_3$ are formed of a shape memory polymer so that they are changed from an oblong shape at a body temperature (36° C.) into a triangular shape at 43° C., and a spherical shape 42° C. and a square shape at 40° C. respectively when they are heated by being irradiated with supersonic wave. They are disposed at diseased part in a human body 10 to conduct hyperthermia treatment. Change in shape of the heat treating member $12a$, ($12a_2$, $12a_3$) is detected from outside of the body by means of supersonic observation apparatus 17 having a supersonic wave probe 17a so that the heating temperature for the diseased part can be read. It is of course that an apparatus for detecting change in shape may use X ray as well as supersonic waves.

If a shape memory member which forms the heat generating members $12a_1$ through $12a_3$ is formed of a wire, change in its shape could be readily detected.

Figure 16:
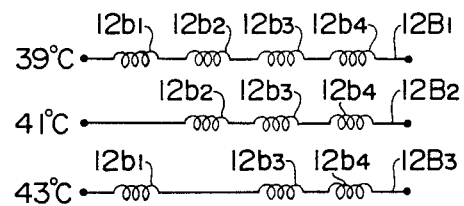
FIG. 16 is a schematic view showing another example of a heat generating member.

FIG. 16 shows heat generating members $12B_1$ through $12B_3$ which are formed of a shape memory member which is in the form of wire. The heat generating member 12B comprises four coils $12b_1$ through $12b_4$ at 39° C. The heat generating member $12B_2$ has a coil $12b_1$ which is changed to rectlinear shape at 41° C. The heat generating member $12B_3$ has a coil $12b_2$ which is changed to rectlinear shape at 43° C. In such a manner shapes are memorized.

Figure 17:
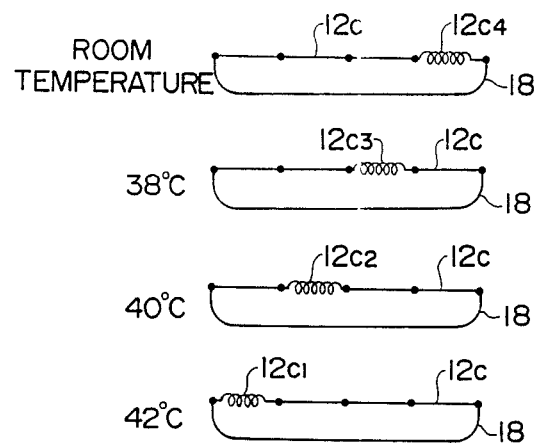
FIG. 17 is a schematic views showing another example of a heat generating member.

A heat generating member 12c may be formed of shape memory wire members having different reaction temperatures which are in series connected between supporting members 18, as shown in FIG. 17. Shapes are memorized in such a manner that a coil $17c_4$ is formed at the right end at room temperature, a coil $12c_3$ is formed at second right end at 38° C., a coil $12C_2$ is formed at the second left end at 40° C. and a coil $12C_1$ is formed at left end at 42° C.

Fine change in temperature can be detected if the coils are made of materials having different reaction temperatures in such a manner.

Figure 18:
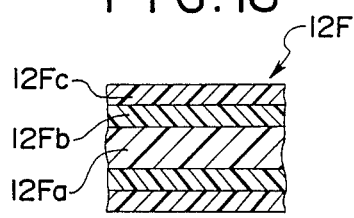
FIG. 18 is an enlarged sectional view showing further example of a heat generating member.

Effective and wide range hyperthermia treatment could be conducted since the whole of a heat generating member 12F is heated by the irradition with supersonic waves if the heat generating member is formed into a short cylinder having a multi-layered structure as shown in FIG. 18. That is, a core $12Fa$ is made of polyethylene, an intermediate layer $12Fb$ surrounding the core is made of natural rubber and an outer layer $12Fc$ covering the outer periphery of the intermediate layer $12Fb$ is made of polystyrene so that the heat generating member is in multi-layered structure and their supersonic wave absorbing characteristics are in a relation; $12Fc < 12Fb < 12Fa$. Since the above mentioned materials have an acoustic characteristics similar to that of living body tissue having an acoustic impedance almost the same as water, the supersonic wave increases the temperature of the heat generating member from outer side to inner side thereof as it transmits through respective materials. Accordingly, effective hyperthermia treatment can be conducted since the whole of a heat generating member 12F including the core portion is heated.

It is better to change the frequency of the supersonic waves depending upon the dimension of the heat generating member and the supersonic wave absorbing characteristics. A heat generating member having a large outer diameter or a heat generating member having a small outer diameter is used depending upon a diseased part position and the size thereof. Supersonic waves having high and low frequencies are used when a heat generating member having a small and large outer diameters is used respectively. It is possible to sufficiently heat even a small heat generating member having a high attenuation if a high frequency supersonic wave is used. In a method of supersonic wave hyperthermia treatment of the present invention, the supersonic wave is pulsatedly transmitted from a supersonic wave generator 6. It is necessary to control the temperature elevated by supersonic waves converged at the heat generating member or the diseased part by suitable means.

In accordance with the present invention, temperature control of a heat generating member is accomplished by detecting the change in temperature of the heating portion and controlling a supersonic oscillator driving circuit in response to a detected signal.

Figure 19:
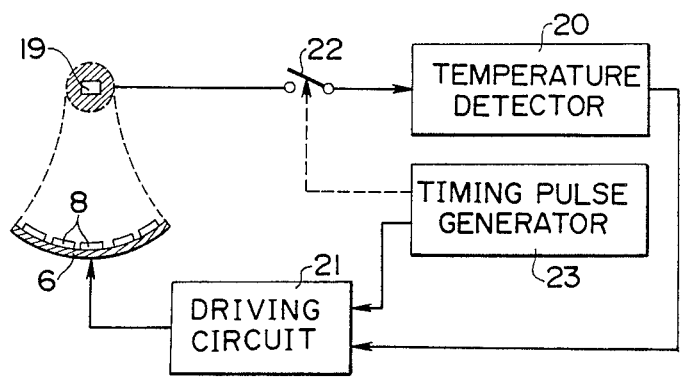
FIG. 19 is a block diagram showing an example of means for controlling the temperature of a heating portion.
Figure 20:
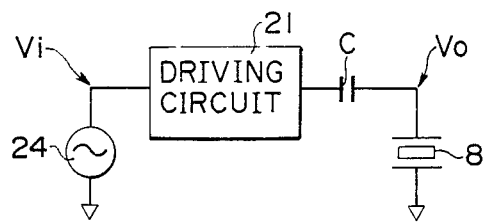
FIG. 20 is a wiring diagram showing an example of means for preventing excessively high output of driving output pulse.

FIG. 19 is a block diagram showing a control system for controlling the temperature. That is, the temperature of a heating portion is detected by a thermal sensor 19. A signal which is obtained by comparing the detected temperature with a predetermined temperature is negatively fed back to a supersonic wave oscillator driving circuit 21 from a thermal detector 20. The temperature is controlled by changing the value of an output voltage of the driving circuit 21 for driving a supersonic wave oscillator 8 of a supersonic wave generator 6, or alternatively by changing the duty cycle of the pulse driving voltage. The thermal sensor 19 is connected with the temperature detector 20 through a switch 22 which is turned off for eliminating noise on transmission of the supersonic wave. The operation of the switch 22 and the driving circuit 21 is controlled by a timing pulse generator 23.

The thus formed temperature control is capable of stably controlling the temperature of the heating portion to a desired preset temperature.

In accordance with the present invention, an output of the supersonic wave oscillator driving circuit 21 to be applied to a supersonic oscillator 8 is so adapted that it will not become excessively high even if some trouble takes place. An output of the supersonic wave oscillator driving circuit 21 to which an output of an oscillator 24 is applied is applied to the oscillator 8 through a direct current eliminating capacitor C. In other words, a maximum amplitude of the output pulse is determined by the direct currect eliminating capacitor for the driving circuit output.

Figure 21A:
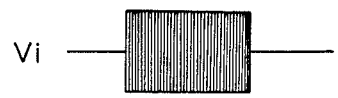
FIGS. 21A and 21B are waveform views showing the output from the circuit shown in FIG. 20.
Figure 21B:
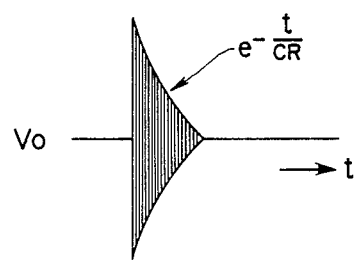

This causes an output Vo to attenuate along an attenuating curve of $$e^{-\frac{1}{CR}}$$

as shown in FIG. 21B even when the amplitude of the pulse becomes excessively high due to trouble in a control system as shown in FIG. 21A if the resistance of the supersonic wave oscillator (piezoelectric element) is represented as R at a driving frequency. Accordingly an excessively high output of the driving circuit is prevented.

What is claimed is:

1. A supersonic hyperthermia treating method comprising the steps of;
   inserting a heat generating member having a high attenuation for supersonic waves into a part to be treated in a body;
   leaving the heat generating member in the part; and
   transmitting supersonic waves from the outside of the body to the heat generating member by means of a supersonic wave generator which generates supersonic waves to cause the heat generating member to heat the part to be treated.

2. A supersonic hyperthermia treating method as defined in claim 1 in which the supersonic wave generator is adapted to focus the generated supersonic waves on the heat generating member.

3. A supersonic hyperthermia treating method as defined in claim 1 in which the heat generating member is formed of a polymeric material of silicon rubber, polyethylene, acrylic resins, or ethylene tetrafluoride.

4. A supersonic hyperthermia treating method as defined in claim 3 for treating a part of an intra-abdominal organ in which the heat generating member made of a polymeric material is shaped according to the organ into which the member is to be inserted and the dimension and position of the part to be treated.

5. A supersonic hyperthermia treating method as defined in claim 1 in which the heat generating member comprises a balloon made of an extensible elastomeric material.

6. A supersonic hyperthermia treating method as defined in claim 5 in which the extensible elastomeric material is latex or silicon rubber.

7. A supersonic hyperthermia treating method as defined in claim 1 in which the heat generating member is formed of a gel material.

8. A supersonic hyperthermia treating method as defined in claim 7 in which the gel material is a silicon gel.

9. A supersonic hyperthermia treating method as defined in claim 1 in which the heat generating member has means for detecting a shift in position of the member from the part to be treated.

10. A supersonic hyperthermia treating method as defined in claim 9 in which the means comprises a layer of material having an acoustic impedance largely different from that of the heat generating member.

11. A supersonic hyperthermia treating method as defined in claim 1 in which the heat generating member is formed of a shape memory member, the shape of which changes with a change in temperature so that the temperature of the heat generating member is readable by detecting the change in shape from the outside of the body.

12. A supersonic hyperthermia treating method as defined in claim 11 in which the shape memory member is formed of a shape memory polymer.

13. A supersonic hyperthermia treating method as defined in claim 12 in which the polymer is a polystyrene resin or a polyurethane resin.

14. A supersonic hyperthermia treating method as defined in claim 1 in which the heat generating member comprises a plurality of connected shape memory members having reacting temperatures different from each other so that the temperature of the heat generating member is readable from the member deformed.

15. A supersonic hyperthermia treating method as defined in claim 1 in which the heat generating member is detachably mounted to the tip end of a body cavity insertion portion of an endoscope, and is inserted into the part to be treated using said endoscope and is then detached from said tip end to leave the heat generating member in such part.

16. A supersonic hyperthermia treating method as defined in claim 15 in which the endoscope has a treating device insertion channel and means inserted in such channel which prevents the heat generating member from detaching and allows the heat generating member to detach by rotating the same.

17. A supersonic hyperthermia treating method as defined in claim 13 in which the preventing means comprises a balloon catheter inserted into the treating device insertion channel at the tip of the endoscope and which is inflated to prevent the heat generating member from detaching and which is deflated to detach the heat generating member.

18. A supersonic hyperthermia treating method as defined in claim 16 in which the preventing means comprises a gripping forceps inserted into the treating device insertion channel and which prevents the heat generating member from detaching by gripping a part of the heat generating member and allows the heat generating member to detach by opening the forceps.

19. A supersonic hyperthermia treating method as defined in claim 1 in which the heat generating member is made of a contracted shape memory member and is mounted on the outer periphery of the tip end of a body cavity insertion portion of an endoscope so that the heat generating member will not normally detach therefrom and so that the heat generating member may be detached by causing warm water to flow through said insertion portion to expand the heat generating member.

20. A supersonic hyperthermia treating method as defined in claim 19 in which the endoscope is a rigid-scope.

21. A supersonic hyperthermia treating method as defined in claim 1 in which the heat generating member comprises a heat generating liquid having a high viscosity which is introduced into a balloon of a balloon type catheter to inflate the balloon which is then inserted into and left at the part to be treated.

22. A supersonic hyperthermia treating method as defined in claim 21 in which the heat generating liquid is castor oil or glycerin.

23. A supersonic hyperthermia treating method as defined in claim 1 in which the heat generating member is made of a heat generating liquid having a high viscosity, the heat generating liquid being inserted into and disposed at the part to be treated through a catheter between both balloons of a double balloon type catheter inserted into the body cavity.

24. A supersonic hyperthermia treating method as defined in claim 23 in which the heat generating liquid is castor oil or glycerin.

25. A supersonic hyperthermia treating method as defined in claim 1 for treating a part of a body cavity in which a guide wire is inserted into the body cavity through a medical instrument and the wire is used as a guide to insert into and leave the heat generating member at the part to be treated.

26. A supersonic hyperthermia treating method as defined in claim 1 in which the heat generating member is made of a contracted shape memory member and is mounted on the outer periphery of the tip end of a catheter so that the heat generating member will not normally detach therefrom and so that the heat generating member may be detached by causing warm water to flow through said catheter to expand the heat generating member.

27. A supersonic treating method as defined in claim 1 further comprising measuring the temperature of the heat generating member using a temperature sensor, generating an electrical control signal representative of the difference between the measured temperature and a preset temperature and using the control signal to control the output of a supersonic oscillator driving circuit used to control the power supplied to the supersonic wave generator to thereby set the temperature of the heat generating member to the preset temperature.

28. A supersonic treatment method as defined in claim 27 in which the control signal is used to control the output voltage of the driving circuit.

29. A supersonic treatment method as defined in claim 27 in which the control signal is used to control the duty cycle of the driving circuit.

* * * * *